US008388343B2

United States Patent
Better et al.

(10) Patent No.: US 8,388,343 B2
(45) Date of Patent: *Mar. 5, 2013

(54) IMPLANTS, TOOLS, AND METHODS FOR SINUS LIFT AND BONE AUGMENTATION

(75) Inventors: Hadar Better, Tel Aviv (IL); Gideon Fostick, Givat Shmuel (IL); Ilan Uchitel, Kefar Saba (IL); Yossi Gross, Moshav Mazor (IL)

(73) Assignee: Maxillent Ltd., Herzliya, IL (US)

( * ) Notice: Subject to any disclaimer, the term of this patent is extended or adjusted under 35 U.S.C. 154(b) by 19 days.

This patent is subject to a terminal disclaimer.

(21) Appl. No.: 12/661,795

(22) Filed: Mar. 24, 2010

(65) Prior Publication Data

US 2010/0255446 A1 Oct. 7, 2010

Related U.S. Application Data

(63) Continuation-in-part of application No. 12/240,353, filed on Sep. 29, 2008, now Pat. No. 7,934,929, and a continuation-in-part of application No. 12/485,199, filed on Jun. 16, 2009, now Pat. No. 8,029,284, and a continuation-in-part of application No. PCT/IL2009/000931, filed on Sep. 29, 2009.

(51) Int. Cl.
*A61C 8/00* (2006.01)
(52) U.S. Cl. ........................................................ 433/174
(58) Field of Classification Search .................. 433/173, 433/174, 229; 606/190
See application file for complete search history.

(56) References Cited

U.S. PATENT DOCUMENTS

| 4,112,944 A | 9/1978 | Williams |
| 4,412,825 A | 11/1983 | Tokarz |
| 4,431,416 A | 2/1984 | Niznick |
| 4,673,353 A | 6/1987 | Nevin |
| 5,049,125 A | 9/1991 | Accaries et al. |
| 5,188,488 A | 2/1993 | Nakayama et al. |
| 5,261,818 A | 11/1993 | Shaw |
| 5,291,914 A | 3/1994 | Bares et al. |
| 5,312,255 A | 5/1994 | Bauer |
| 5,456,601 A | 10/1995 | Sebdax |
| 5,481,260 A | 1/1996 | Buckler et al. |
| 5,575,650 A | 11/1996 | Niznick et al. |
| 5,584,688 A | 12/1996 | Sakuma et al. |
| 5,685,716 A | 11/1997 | Linkow |
| 5,711,315 A | 1/1998 | Jerusalmy |
| 5,759,036 A | 6/1998 | Hinds |
| 5,782,918 A | 7/1998 | Klardie et al. |
| 5,795,160 A | 8/1998 | Hahn et al. |

(Continued)

FOREIGN PATENT DOCUMENTS

| EP | 1174094 | 1/2002 |
| EP | 1174094 A1 | 1/2002 |

(Continued)

OTHER PUBLICATIONS

An Office Action dated Apr. 11, 2011, which issued during the prosecution of Applicant's U.S. Appl. No. 12/485,199.

(Continued)

*Primary Examiner* — Ralph Lewis
(74) *Attorney, Agent, or Firm* — Fish & Richardson P.C.

(57) ABSTRACT

A minimally-invasive sinus lift implant and implantation methods are disclosed. An implant apparatus may included an anchor having a distal implant end and an opposite proximal end. The implant apparatus may further include a channel extending though a portion of the anchor and having an outlet opening in the distal implant end. The channel may also include an inlet opening on a side of the anchor between the distal implant end and the proximal end. Further, the inlet opening, the channel, and the outlet opening may be configured to convey fluid therethrough and the implant is configured for implantation in a bone such that when fully implanted, the side inlet opening is buried in the bone.

30 Claims, 10 Drawing Sheets

U.S. PATENT DOCUMENTS

| | | | |
|---|---|---|---|
| 5,829,977 | A | 11/1998 | Rogers et al. |
| 5,839,899 | A | 11/1998 | Robinson |
| 5,879,161 | A | 3/1999 | Lazzara |
| 5,915,967 | A | 6/1999 | Clokie |
| 5,967,777 | A | 10/1999 | Klein et al. |
| 5,989,025 | A | 11/1999 | Conley |
| 6,068,479 | A | 5/2000 | Kwan |
| 6,159,161 | A | 12/2000 | Hodosh |
| 6,200,289 | B1 | 3/2001 | Hochman |
| 6,273,720 | B1 | 8/2001 | Spalten |
| 6,758,673 | B2 | 7/2004 | Fromovich et al. |
| 7,100,476 | B1 | 9/2006 | Feit |
| 7,217,130 | B2 | 5/2007 | Giorno |
| 7,297,102 | B2 | 11/2007 | Smith et al. |
| 7,364,430 | B2 | 4/2008 | Kitamura et al. |
| 7,396,232 | B2 | 7/2008 | Fromovich et al. |
| 7,510,397 | B2 | 3/2009 | Hothman |
| 7,934,929 | B2 * | 5/2011 | Better et al. .................. 433/174 |
| 8,029,284 | B2 * | 10/2011 | Better et al. .................. 433/173 |
| 2003/0105469 | A1 | 6/2003 | Karmon |
| 2003/0175656 | A1 | 9/2003 | Livne et al. |
| 2003/0228556 | A1 | 12/2003 | Giorno |
| 2003/0232308 | A1 | 12/2003 | Simmons |
| 2006/0020326 | A9 | 1/2006 | Bolduc et al. |
| 2006/0084034 | A1 | 4/2006 | Hochman |
| 2006/0172255 | A1 | 8/2006 | Hochman et al. |
| 2007/0055257 | A1 | 3/2007 | Vaccaro |
| 2007/0162024 | A1 | 7/2007 | Siemonsmeier |
| 2008/0108011 | A1 | 5/2008 | Nahlieli |
| 2008/0213729 | A1 | 9/2008 | Hochman |
| 2008/0215010 | A1 | 9/2008 | Silver et al. |
| 2008/0319466 | A1 | 12/2008 | Eder |
| 2010/0047733 | A1 | 2/2010 | Nahlieli |
| 2010/0081111 | A1 | 4/2010 | Better et al. |
| 2010/0081112 | A1 | 4/2010 | Better et al. |
| 2010/0196841 | A1 | 8/2010 | Nahlieli et al. |
| 2010/0324561 | A1 | 12/2010 | Watzek et al. |

FOREIGN PATENT DOCUMENTS

| | | |
|---|---|---|
| WO | WO2007007331 A1 | 1/2007 |
| WO | 2007080595 | 7/2007 |
| WO | 2007114553 | 10/2007 |
| WO | WO2007114553 A1 | 10/2007 |
| WO | WO2007080595 A3 | 4/2009 |
| WO | 2010035270 | 4/2010 |
| WO | WO2010035270 A3 | 5/2010 |
| WO | WO2010146573 A1 | 12/2010 |

OTHER PUBLICATIONS

Sotirakis E, "A different method for elevation of the floor of the maxillary sinus: Experimental study and reference to some cases", Mediterranean Dental Implant Congress (Athens, Greece), Scientific programme MDIC 2004—an abstract.

Chen L et al., "An 8-year retrospective study: 1,100 patients receiving 1'557 implants using the minimally invasive hydraulic sinus condensing technique" J Periodontol 76:482-491, 2005.

Muronoi M et al., "Simplified procedure for augmentation of the sinus floor using a haemostatic nasal balloon", British Journal of Oral & Maxillofacial Surgery 41(2): 120-121, 2003.

Vercellotti T, "Piezoelectric surgery in implantology: a case report—a new piezoelectric ridge expansion technique", Int J Periodontics Restorative Dent 20(4): 358-65, 2000—an abstract.

Vercellotti T, "The Piezoelectric bony window osteotomy and sinus membrane elevation: Introduction of a new technique for simplification of the sinus augmentation procedure", Int J Periodontics Restorative Dent 21(6): 561-7, 2001—an abstract.

Flanagan D, "Important arterial supply of the Mandible, Control of an Arterial Hemorrhage, and Report of a Hemorrhagic Incident", J Oral Implantol 29(4): 165-73, 2003.

A Brochure: "Sincrest Technique—A Different Way", by Meta, Italy. www.metashop.com.

U.S. Appl. No. 60/619,542, Oct. 2004.

Riley ET et al., "The Episure syringe: a novel loss of resistance syringe for locating the epidural space," Anesth Analg. 105(4): 1164-6 (Oct. 2007).

An International Preliminary Report on Patentability dated Dec. 16, 2011, which issued during the prosecution of Applicant's PCT/IL10/00252.

An Office Action dated Jun. 28, 2012, which issued during the prosecution of U.S. Appl. No. 13/040,440.

* cited by examiner

IMPLANTS, TOOLS, AND METHODS FOR SINUS LIFT AND BONE AUGMENTATION

CROSS-REFERENCE TO RELATED APPLICATIONS

This application is a Continuation-in-Part of: (a) U.S. application Ser. No. 12/240,353, filed Sep. 29, 2008, entitled "Sinus lift implant," to Better et al., now U.S. Pat. No. 7,934,929, (b) U.S. application Ser. No. 12/485,199, filed Jun. 16, 2009, entitled, "Implants, tools, and methods for sinus lift and lateral ridge augmentation," to Better et al., now U.S. Pat. No. 8,029,284, and (c) International Application No. PCT/IL2009/000931, filed Sep. 29, 2009, entitled, "Implants, tools, and methods for sinus lift and lateral ridge augmentation," to Better et al., which published as PCT Publication WO 2010/035270, all of which are assigned to the assignee of the present application and are incorporated herein by reference in their entirety.

FIELD OF TECHNOLOGY

The presently disclosed embodiments relate generally to implants and implantation methods, and may involve, for example, minimally-invasive sinus lift implants and implantation methods.

BACKGROUND

Osseointegrated implants are typically metallic or ceramic screws that may be placed in a bone of a patient for supporting a prosthesis. For example, an osseointegrated implant may include a dental implant for insertion into a jawbone of a patient. Such an implant may support an artificial tooth after the loss of a natural tooth. Replacement of a tooth is often a challenging surgical procedure when the remaining bone has insufficient height to support the implant. For example, replacement of the maxillary teeth is often a challenging surgical procedure when the remaining maxillary bone has insufficient height to support the implant. One surgical technique for augmenting the maxillary bone includes introducing a regenerative material, such as autogenic, allogeneic, xenogeneic, or synthetic bone graft, into the vicinity of the maxillary bone. The regenerative material may form additional bone mass that may integrate with the existing maxillary bone, providing the necessary alveolar height to support the implant.

Bone augmentation procedures are often surgically difficult to perform, and are associated with complications, including infection of the maxillary sinus. The top of the maxillary alveolar ridge forms the floor of the maxillary sinus, and is covered by a thin membrane known as the Schneiderian or subantral membrane. In one surgical procedure, known as a closed or internal sinus lift or elevation procedure, the surgeon drills a bore through the maxillary alveolar ridge from the oral cavity at the desired location of the implant. The bore penetrates the ridge to below the Schneiderian membrane. The surgeon injects the regenerative material through the bore to below the membrane, forming a cavity defined by the top of the ridge and the bottom of the membrane, which cavity occupies a portion of the space initially occupied by the maxillary sinus.

To prevent potentially serious complications, the surgeon must be careful not to perforate the Schneiderian membrane. This is often difficult, because of the delicacy of the membrane, and the restricted access afforded by the closed approach.

Various techniques have been developed to augment bones. One such technique includes a method of lifting a membrane using hydraulic pressure applied by a syringe. A second such technique requires the use of various sinus burs and condensers of increasing width in conjunction with a pliable atraumatic bone grafting mixture and hydraulic pressure from a surgical hand piece. A third technique includes the use of a sleeve to raise the subantral membrane and form a cavity. A filler, such as a bone growth stimulant, may be injected through the sleeve into the cavity. In the process, the sleeve may also cut and/or condense the bone around itself so that the bone may hold an implant. Optionally, the bone growth stimulant may be introduced into the bone surrounding the sleeve. During the injection, the pressure within the sleeve or the cavity may be monitored to detect and prevent the rupture of the subantral membrane.

Further techniques include the use of surgical tools to cut, crack, and push bone from the sinus floor upward into the sinus cavity in a controlled motion. Once the bony sinus floor is cracked free, a fluid passageway may be pressurized with a sterile fluid at a defined pressure to release and push the sinus membrane upward into the sinus cavity which may create a desired apical cavity for grafting. Alternatively, such tools may provide a passageway for carrying fluid through the shank of the tool. Another technique includes the use of an implant comprising at least one shaft area for anchoring in a bony structure, and at least one opening at the distal end of the shaft area in which the shaft area may have a continuous bore extending from the opening to at least one outlet at the apical end, so that targeted introduction of material at least into the periapical area is possible with a stable anchoring in the bone structure even after implantation. Finally, techniques have been developed which may gradually displace periosteal tissue covering bones. The gap developing between the bone and the displaced periosteal tissue may be filled with bone callus as it is in distraction osteogenesis. The techniques allow formation of bone in distraction osteogenesis without cutting a segment of the bone.

Although the above techniques may improve the ability to augment a bone, such techniques may be very complex, invasive, and painful. They may require a very long recovery time and result in temporary disfiguration. Also, patients may experience a high risk of complications, including, for example, tearing of the Schneiderian membrane and infection. Further, such techniques may often be practiced only by very experienced specialists in the maxillofacial field.

SUMMARY

In one exemplary embodiment of the invention, an implant apparatus includes an anchor having a distal implant end and an opposite proximal end. The implant apparatus may further include a channel extending though a portion of the anchor and having an outlet opening in the distal implant end. The channel may also include an inlet opening on a side of the anchor between the distal implant end and the proximal end. Further, the inlet opening, the channel, and the outlet opening may be configured to convey fluid therethrough and the implant may be configured for implantation in a bone such that when fully implanted, the side inlet opening is buried in the bone.

In another disclosed embodiment, the implant apparatus may further include a channel extending though a portion of the anchor in a generally longitudinal direction of the anchor, the channel extending though only a portion of the anchor, from a side inlet opening to the outlet opening on the distal end. The inlet opening, the channel, and the outlet opening may be configured to convey fluid there though.

In a further disclosed embodiment, an implant method includes drilling a hole in a maxillary bone, and inserting an implant into the hole. Depending on intended use, the implant may be configured such that upon insertion it forms a substantially liquid tight seal between the implant and the maxillary bone. The implant method may further include lifting a Schneiderian membrane by introducing fluid through a channel in the implant such that the fluid contacts the Schneiderian membrane and exerts a force thereon, causing a space between the maxillary bone and the Schneiderian membrane. The implant method may also include draining the fluid from the space via the channel in the implant and conveying bone regenerative material through the channel and into the space.

The drawings and detailed description which follow contain numerous alternative examples consistent with the invention. A summary of every feature disclosed is beyond the object of this summary section. For a more detailed description of exemplary aspects of the invention, reference should be made to the drawings, detailed description, and claims, which are incorporated into this summary by reference.

It is to be understood that the forgoing summary addresses only a few exemplary aspects of the invention, and that both the foregoing general description and the following detailed description are exemplary and explanatory only and are not restrictive of the invention, as claimed.

DESCRIPTION OF EXEMPLARY EMBODIMENTS

Reference will now be made in detail to exemplary embodiments of the invention, examples of which are illustrated in the accompanying drawings. Wherever possible, the same reference numbers will be used throughout the drawings to refer to the same or like parts.

Figure 1A:
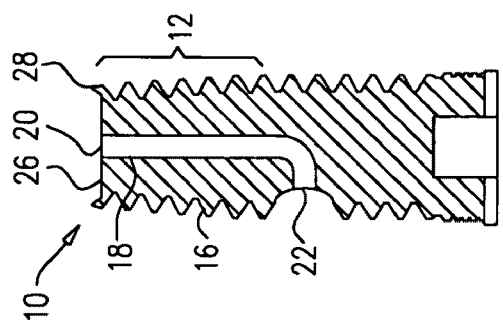
FIG. 1A provides a diagrammatic representation of an anchor in accordance with an exemplary disclosed embodiment.

FIG. 1A illustrates an exemplary anchor 10 in accordance with one disclosed embodiment. Anchor 10 may have an elongated shape with a distal implant end 12 and opposite proximal end 14. At least a portion of anchor 10 may be appropriately configured for insertion into a bone of a patient. While the bone in which anchor 10 may be inserted may include any human or animal bone, for purposes of discussion only, various anchors are discussed herein for use in human jaw or maxillary bones. It is to be understood that this exemplary description is not intended to limit the invention in its broadest sense. While anchor dimensions and shapes may be a function of intended use, and while the invention in its broadest sense is not limited to particular dimensions and shapes, exemplary anchors in accordance with embodiments of the invention may include cylindrical, tapered, and/or conical shapes, and may include structures having, for example, circular or oval cross-sections. Exemplary anchors in accordance with embodiments of the invention may have a greatest diameter, for example, of between about 2 mm and about 7 mm, and may be provided in a variety of longitudinal lengths. In certain embodiments these anchors may have longitudinal lengths of, e.g., between about 7 mm and about 18 mm. More particularly, such anchors may have longitudinal lengths of, e.g., between about 12 and about 16 mm, or even more particularly of about 15 mm. For exemplary purposes only, anchor 10 may have a longitudinal length of about 14 mm, about 15.5 mm, or about 18 mm, or other lengths between about 14 mm and 18 mm. For some applications, anchor 10 may have a longitudinal length of less than about 20 mm and a greatest diameter of less than about 10 mm. The diameter of anchor 10 may be substantially constant or may vary along its longitudinal length. Anchor 10 may be constructed of any biocompatible material of sufficient strength and durability to withstand insertion into a bone of a patient. By way of example only, anchor 10 may be made of a metal such as titanium or stainless steel, a composite, a plastic, a synthetic, or a ceramic, such as a zirconia (zirconium dioxide) ceramic.

Depending on the intended application, anchor 10 may include external threads 16 for permitting the anchor to be screwed into bone. Anchor 10 may further include tapping and milling elements 64 and 66, respectively, as discussed later in greater detail with reference to FIGS. 4A-4B.

Proximal end 14 of anchor 10 may be configured to permit a prosthesis to be connected thereto. For example, when anchor 10 is configured for insertion in a maxillary or jaw bone, proximal end 14 may be configured to support a prosthetic tooth. For other uses, differing prosthetics and other attachments may be connectable to proximal end 14 via mechanical, magnetic, or adhesive connection. Such connecting features may include, for example, internal hexagonal connections, external hexagonal connections, other anti-rotational connections, external screw threads, internal screw threads, lock nut constructions, friction fittings, bayonet type mounts, pin connectors, eyelets, or any other structure that permits secure mechanical connection to anchor 10. Alternatively, a magnet may be implanted in anchor 10 or the anchor may provide a connection surface to which a structure may be banded, clamped or adhered. It is to be understood that the invention is not limited to anchors 10 with particular connecting features. Rather, if a connecting feature is desired in accordance with an embodiment of the invention, the details of that feature may be chosen to fit the intended application.

In accordance with one embodiment of the invention there may also be provided a channel extending through a portion of the anchor. As illustrated in FIG. 1A, for example, a channel 18 may extend from an inlet opening 22 in a side of anchor 10, through at least a portion of anchor 10, to an outlet opening 20 on distal implant end 12. Alternatively, by way of example only, channel 18 may terminate at distal implant end 12 in a plurality of outlet openings 20, as represented in by the exemplary embodiment of FIG. 1B. Channel 18 may be configured so as to convey fluid from inlet opening 22 to outlet opening 20.

Channel 18 may be formed so as to be coaxial with a central axis 24 of anchor 10. Alternatively, channel 18 may be formed so as to be offset from central axis 24. Channel 18 may be configured in any cross-sectional shape or combination of shapes capable of conveying fluid therethrough. Thus, by way of non-limiting example, channel 18 may include a cross-section that is circular, square, rectangular, triangular, or any other cross-sectional shape capable of conveying fluid.

As shown in FIG. 1A, channel 18 may extend in a generally longitudinal direction of anchor 10, from distal implant end 12 towards proximal end 14. Furthermore, inlet opening 22 may be spaced from the proximal-most end of anchor 10. As such, channel 18 may be configured to extend through only a portion of anchor 10, from the side inlet opening 22 to the outlet opening 20 on the distal implant end 12.

Figure 1B:
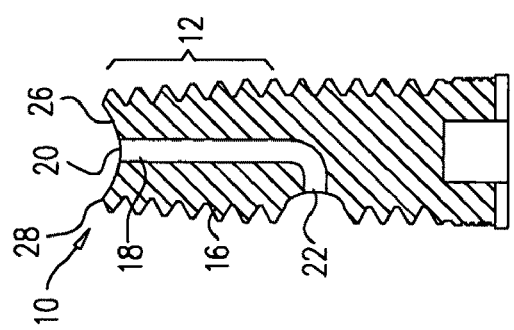
FIG. 1B provides a diagrammatic representation of an anchor in accordance with another exemplary disclosed embodiment.
Figure 1C:
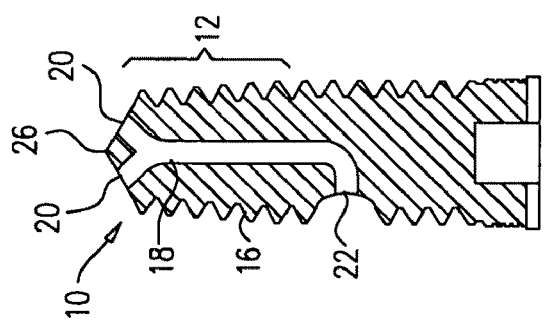
FIG. 1C provides a diagrammatic representation of an anchor in accordance with another exemplary disclosed embodiment.
Figure 1D:
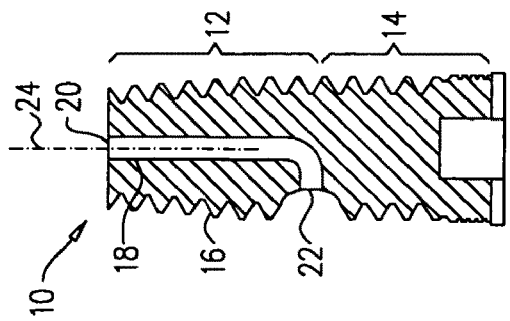
FIG. 1D provides a diagrammatic representation of an anchor in accordance with another exemplary disclosed embodiment.

Reference is made to FIGS. 1B-D, which are diagrammatic illustrations of additional exemplary configurations of anchor 10. In the configuration shown in FIG. 1B, outlet openings 20 of channel 18 may be located on distal implant end 12 at a location other than coincident with a distal-most tip 26 of anchor 10. For example, outlet openings 20 may include a plurality of outlet openings 20, and each may be located at a position of within about 3 mm from distal-most tip 26 of anchor 10, as measured along the outer surface of anchor 10. While FIG. 1B shows a plurality of outlet openings 20, certain embodiments may include only a single outlet opening 20. In such an embodiment, outlet opening 20 may be located at a position other than coincident with distal-most tip 26, but within about 3 mm of distal-most tip 26 as measured along the outer surface of anchor 10.

As depicted in FIG. 1C, the distal-most tip 26 of anchor 10 may be configured to include a concave profile. In certain embodiments, a raised edge formed by the perimeter of the concave region may define a sharp cutting surface 28.

Alternatively, as shown in FIG. 1D, the distal-most tip 26 of anchor 10 may be generally flat. Like the embodiment of FIG. 1C, however, the embodiment represented by FIG. 1D may also include a sharp cutting surface 28 formed at or near the perimeter edge of distal-most tip 26 of anchor 10.

In the configurations shown in FIGS. 1C and 1D, outlet opening 20 of channel 18 may include a single outlet opening 20 which may be coincident with distal-most tip 26. Alternatively, outlet opening 20 may be at a location other than coincident with distal-most tip 26 of anchor 10, but within about 3 mm from distal-most tip 26 as measured along the outer surface of anchor 10. Further, outlet opening 20 may include a plurality of outlet openings 20, and each may be located at a position of within about 3 mm from distal-most tip 26 of anchor 10, as measured along the outer surface of anchor 10.

As noted above, anchor 10 may be configured for implantation into a bone of a patient. Anchor 10 may be configured to assume a partially-implanted orientation and/or a fully implanted orientation. While in the partially implanted orientation, side inlet opening 22 may be configured to protrude from the bone of implantation so as to permit access to channel 18. Depending on the intended application, anchor 10 may be configured with a length sufficient to pass through a distal-most side of a bone of implantation while side inlet opening 22 protrudes from the proximal-most side of the bone. In this manner, open channel 18 may exist from inlet opening 22 on the proximal-most side of the bone of implantation to outlet opening 20 on the distal-most side of the bone of implantation (see, e.g., FIG. 5C).

Figure 5A:
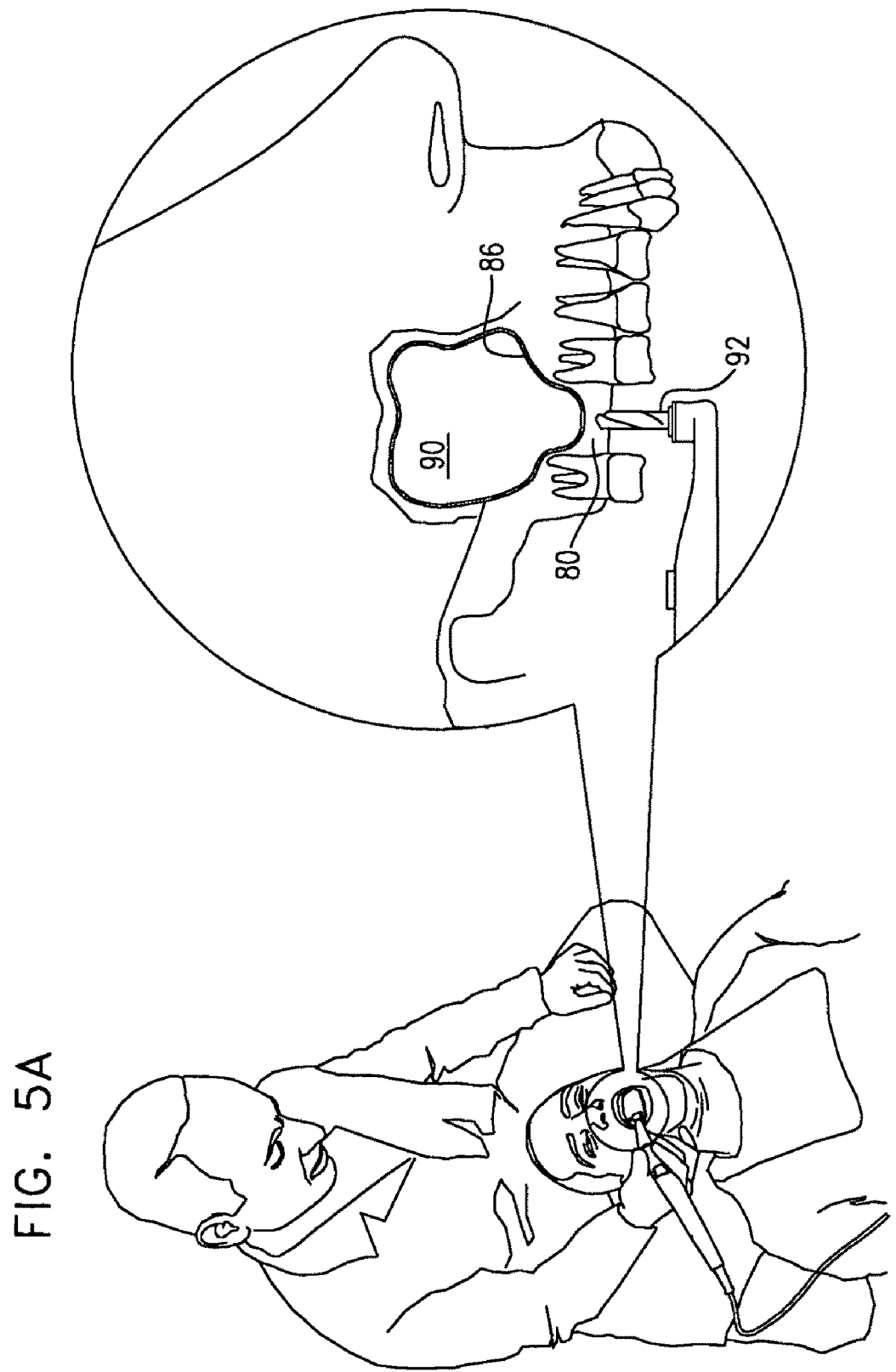
FIGS. 5A-5F represent an exemplary implantation method.
Figure 5B:
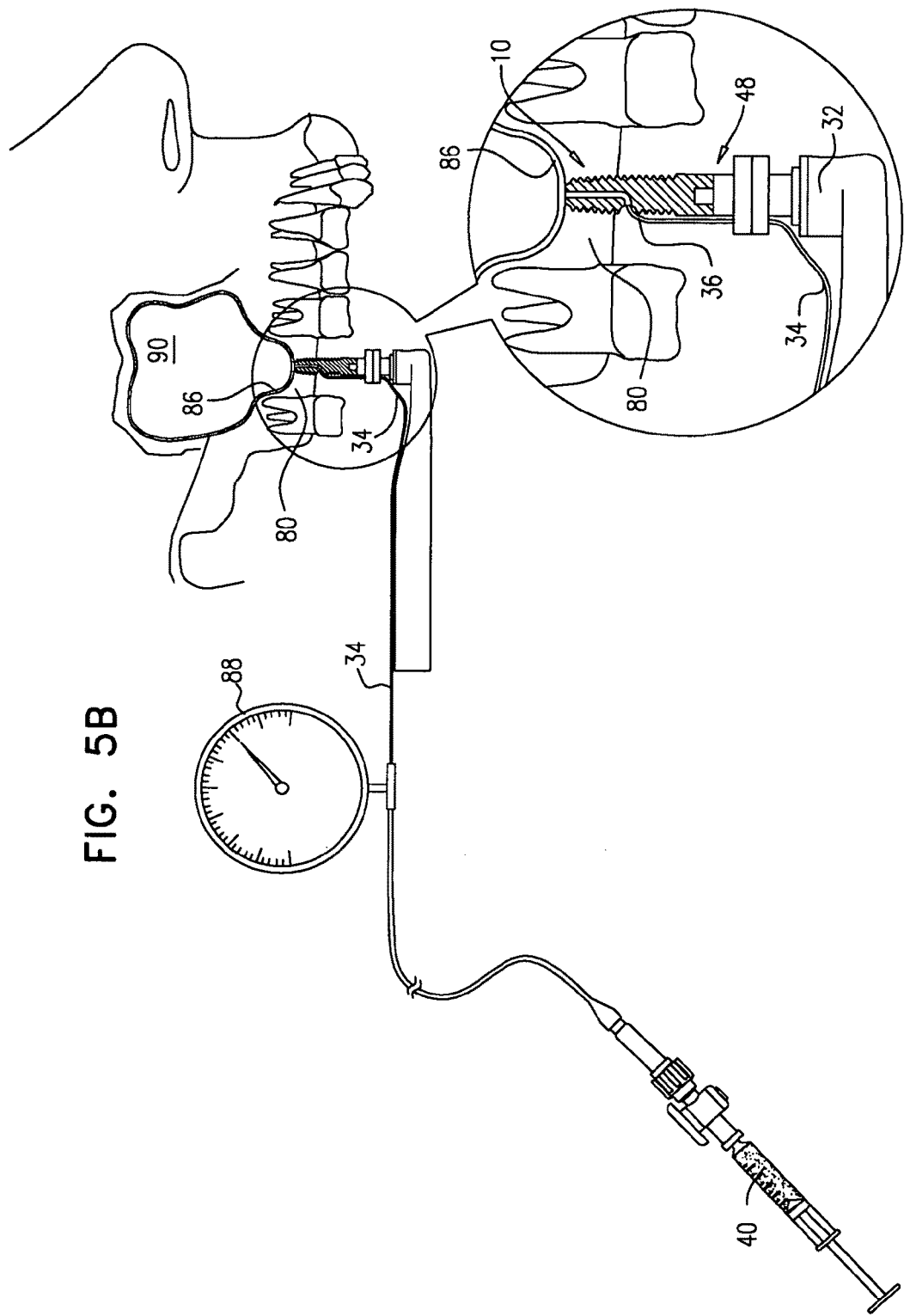
Figure 5C:
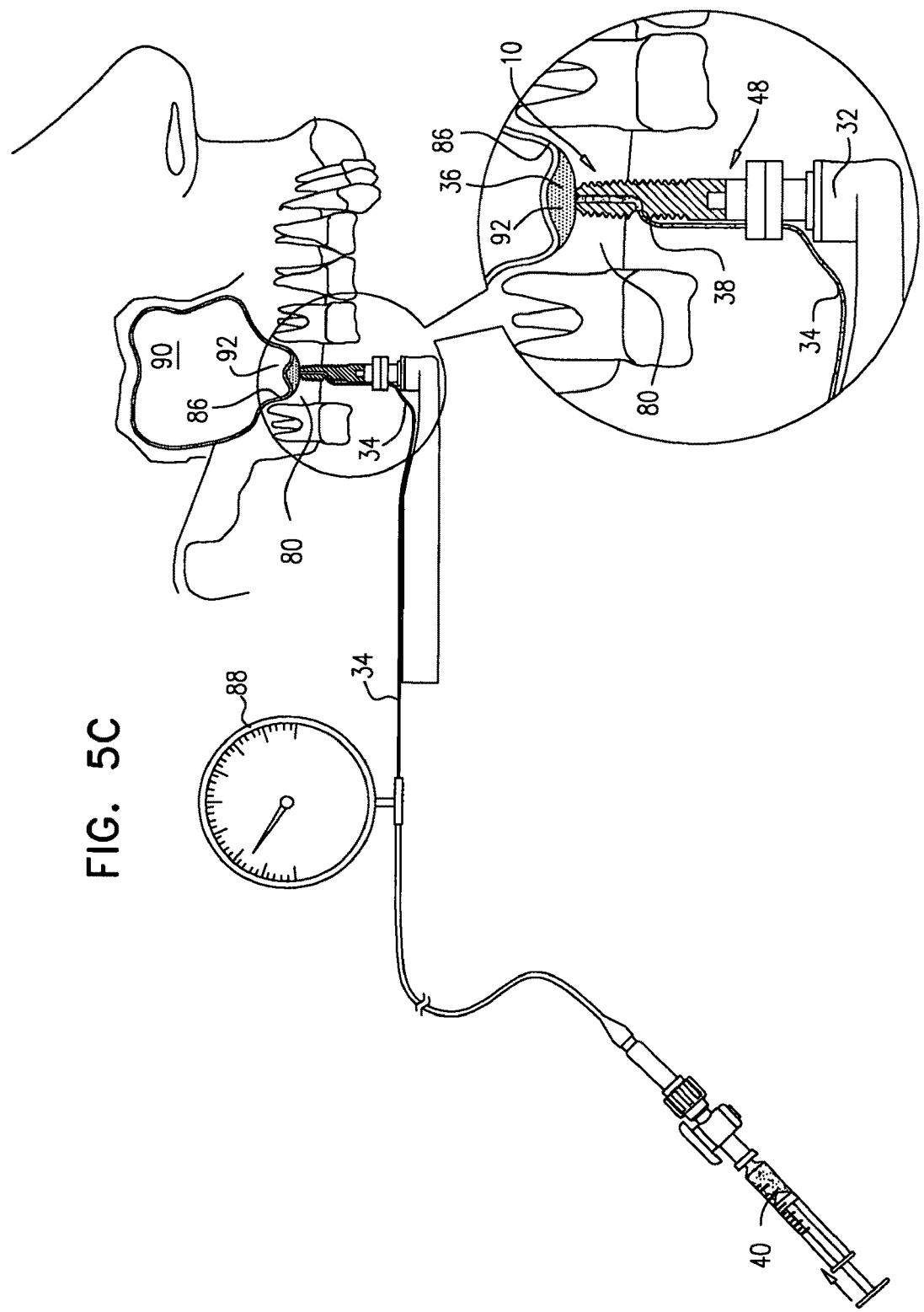
Figure 5D:
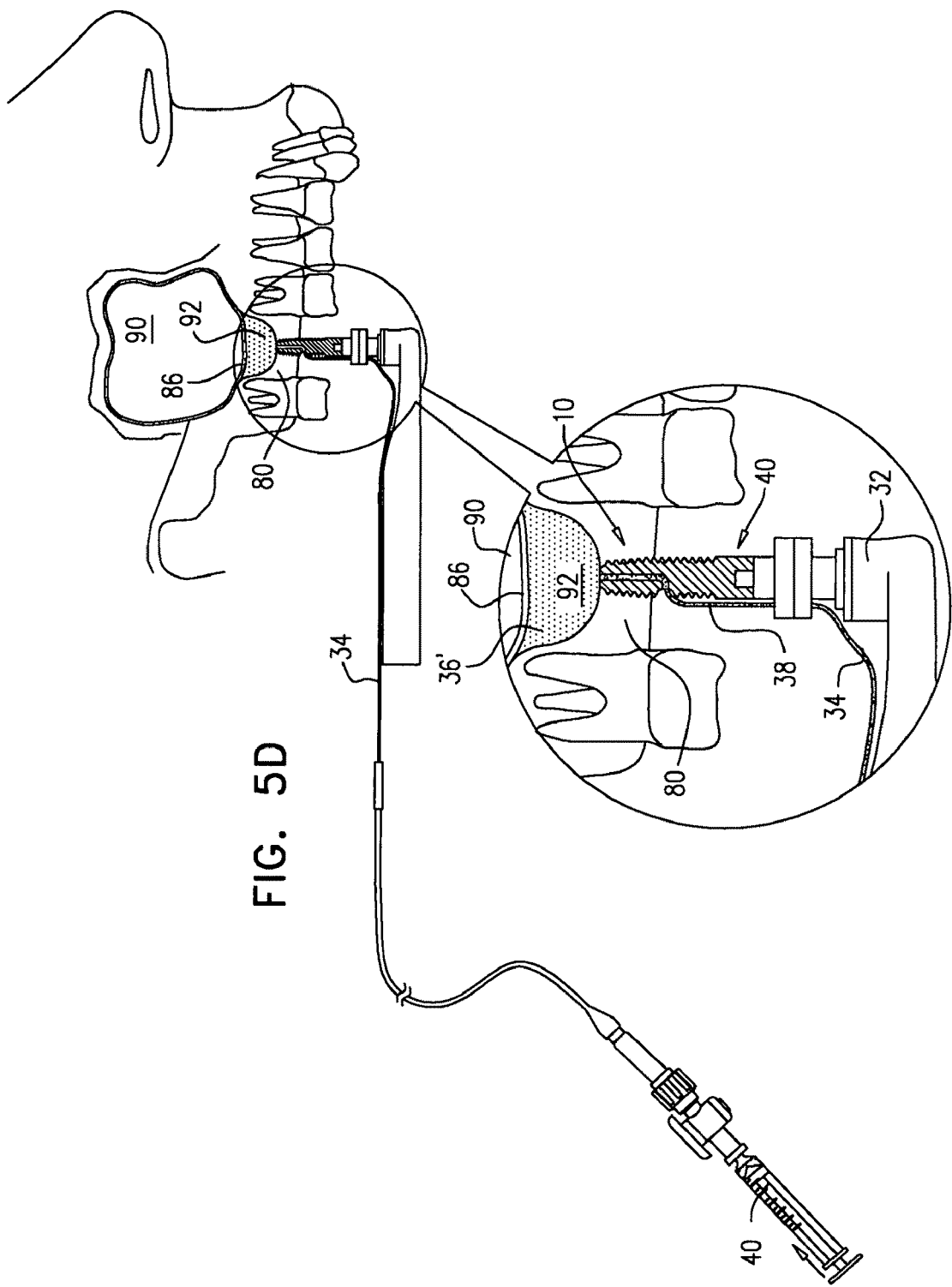
Figure 5F:
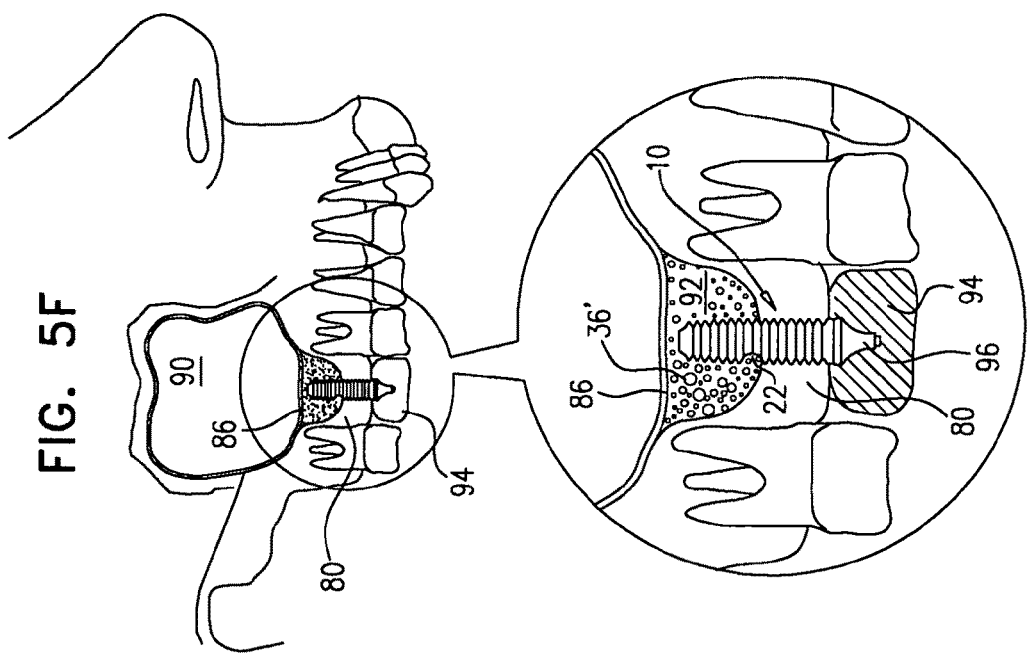
Figure 5E:
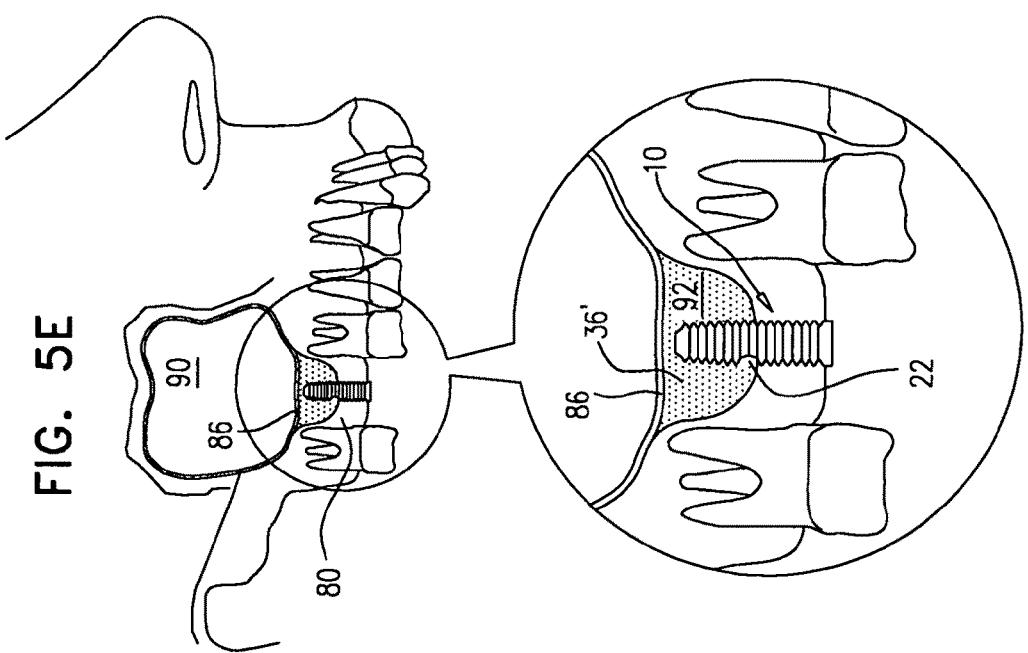

Anchor 10 may be further constructed such that when in a fully-implanted orientation, side inlet opening 22 may be buried in the bone of implantation to block inlet access to channel 18 (see, e.g., FIG. 5E). That is, the inlet opening may be located beneath the outer surface of the bone; may be located within a mass of bone augmenting material within the bone or on a side of the bone opposite the side of implantation; or may be exposed on a side of the bone opposite a side of implantation. In one exemplary embodiment, anchor 10 may be configured such that side inlet opening 22 may be located at a depth of at least 1 mm within the bone of a patient when in the fully-implanted orientation. Alternatively, while in the fully-implanted orientation, side inlet opening 22 may be located at a depth of at least about 3 mm within the bone of a patient. In still other embodiments, anchor 10 may be configured such that side inlet opening 22 may be located at a depth of between about 0-3 mm within the bone of a patient. Further still, anchor 10 may be configured for any depth of burial of side inlet opening 22, depending on the bone for which anchor 10 is constructed and the intended application. In certain embodiments, when anchor 10 is fully inserted into the bone of the patient, side inlet opening 22 of channel 18 may be permanently closed thus blocking access to the interior of the bone of the patient through anchor 10 from the exterior of the bone of the patient thereby reducing the risk of infection.

Figure 2:
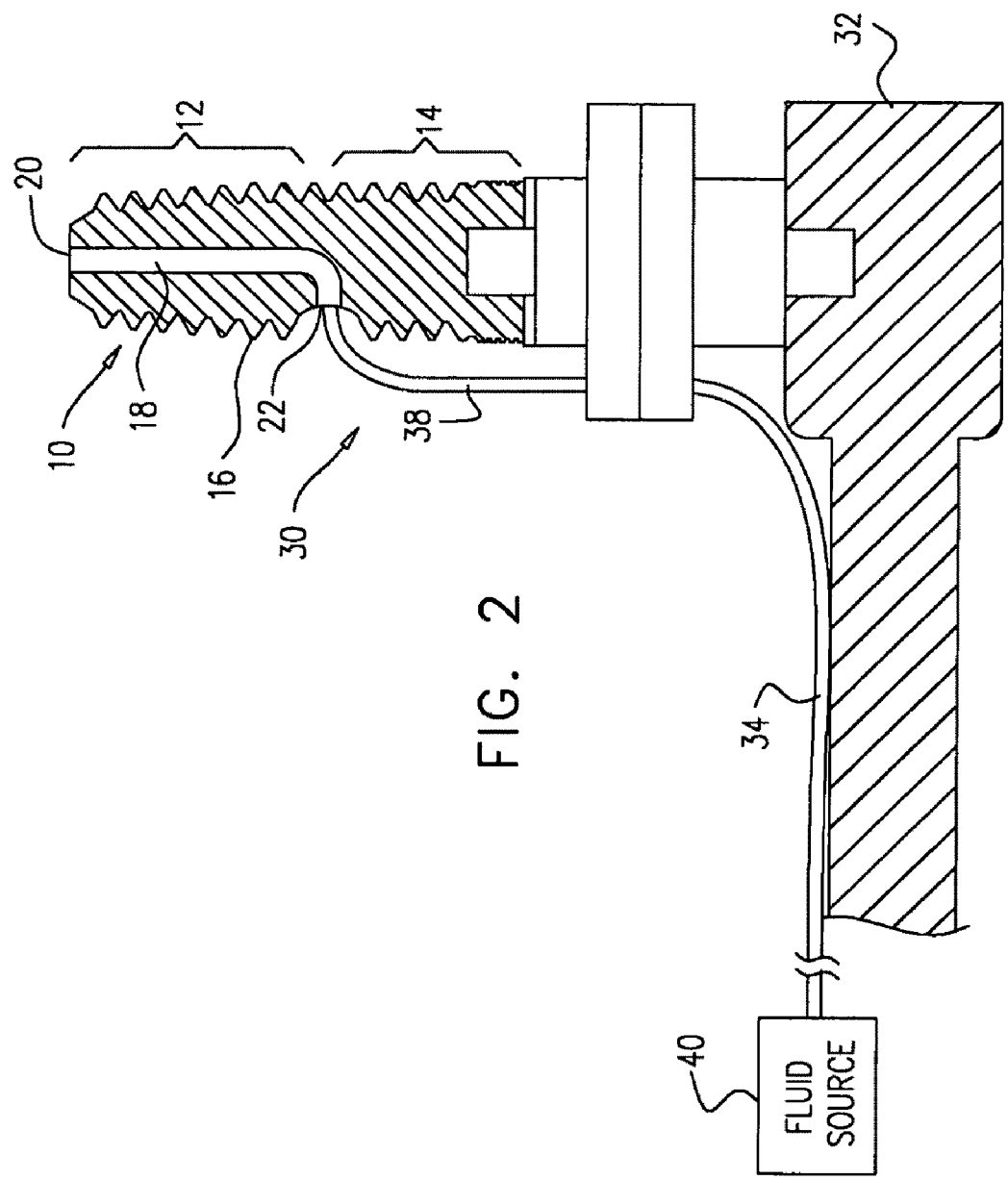
FIG. 2 provides a diagrammatic representation of an exemplary implant apparatus/system.

In accordance with one embodiment of the invention there may be provided an exemplary apparatus/implant system 30 as shown in FIG. 2. System 30 may be used during implantation of anchor 10 into a bone of a patient. System 30 may include any appropriate structure configured to aid in the insertion of anchor 10 into the bone of a patient including, for example, any appropriate electrical or mechanical tooling (e.g., a wrench, surgical screwing tool, etc.) which may be attached to proximal end 14 of anchor 10. The system may further include a connection to a fluid source to supply sufficient fluid such that, upon insertion into the bone of the patient, the fluid may be directed through channel 18 and into the patient. The introduction of fluid may lift a membrane of the patient located on the distal-most surface of the bone in order to create a cavity between the membrane and the bone of the patient. This cavity may remain filled by the fluid, drained and left empty, or drained and filled with a second fluid. The formed cavity and/or the fluid remaining in the cavity, if any, may induce bone growth within the cavity. Such bone growth may aid in supplementing the existing bone of the patient which may thereby improve the ability of a surgeon to insert an anchor into the bone of the patient.

The apparatus/system 30 may include anchor 10, as described hereinabove, and a tool, such as a surgical screwing tool 32. The surgical screwing tool may be attached to anchor 10 via any appropriate intermediate element, such as, for example, an applicator 48 as described hereinbelow with reference to FIG. 3A. Surgical screwing tool 32 may be configured to attach to proximal end 14 of anchor 10 and may aid in insertion of anchor 10 into the bone of the patient. For example, surgical screwing tool 32 may comprise a conventional manual ratchet wrench, or a conventional drill or motor to which an appropriate drill head is attached, and may be operated at a controlled speed and at controlled torque. Alternatively, any appropriate tool known in the art may be used to advance anchor 10 into the bone of the patient.

Further, the apparatus/system 30 may include an inlet conduit 34 configured to direct a fluid 36 (labeled in FIGS. 5B-C) into channel 18 through side inlet opening 22. An exemplary inlet conduit 34 is shown in FIG. 2. Inlet conduit 34 may be of any cross-sectional shape, length and/or size capable of conveying fluid 36 from an external source, through side inlet opening 22, and to channel 18. Inlet conduit 34 may include a delivery tube 38 in which the distal end of delivery tube 38 may be connected to side inlet opening 22.

As shown in FIG. 2, a distal end of inlet conduit 34 may be connected to a container 40. Further, container 40 may be configured to store fluid 36 and may be of any shape or size appropriate to hold sufficient quantities of fluid 36 as may be dictated by the specific application. Alternatively, container 40 may include any commercially available syringe or powered drug delivery device capable of delivering fluid 36 to channel 18 through side inlet opening 22. As used herein, "fluid" may refer to, by way of non-limiting example, any one of or a combination of saline solution, water, bone growth stimulation factors such as bone morphogenic protein ("BMP"), blood, bone graft, bone regenerative material, bone augmenting material, an allograph, an autogeneous bone graft, a xenograft, or any other flowable biocompatible material. Further, fluid 36 may, for example, comprise a natural material, a synthetic material, or a mixture thereof. For example, fluid 36 may include one of the following commercially available fluid bone graft materials: DBX Paste (MTF), Allomatrix (Wright), Cerament (Bone Support), DynaGraft (Citagenix/ISOTIS), Fisiograft (Ghimas), Grafton DBM Gel (Osteotech), Optium DBM Gel (Lifenet/Depuy J&J), OsteoMax (Orthfix), PD VitalOs Cemen (VitalOs), or Regenafil® (Exactech).

After delivery of fluid 36 into the patient through the delivery tube 38, the surgeon may decouple delivery tube 38 from anchor 10 before further inserting anchor 10 into the bone of the patient to bring side inlet opening 22 into a blocked position, such as entirely within the bone of the patient. Alternatively, the surgeon may advance the anchor 10 into the patient such that side inlet opening 22 is within the formed cavity. Such positioning of side inlet opening 22 may substantially reduce the risk of infection because the only portion of anchor 10 exposed to the oral cavity of the patient is permanently closed.

Figure 3A:
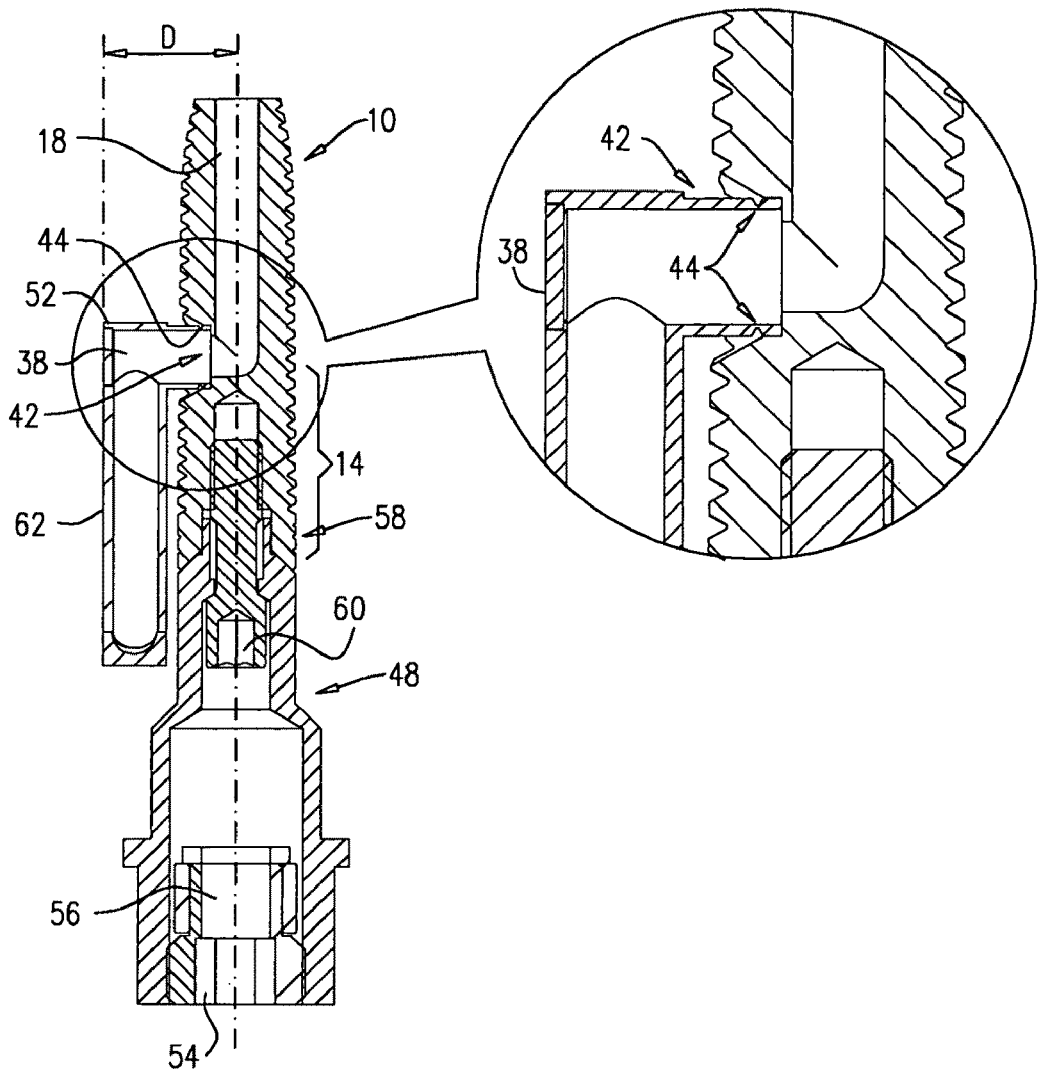
FIG. 3A provides a diagrammatic representation of an exemplary anchor including a delivery tube and applicator.
Figure 3B:
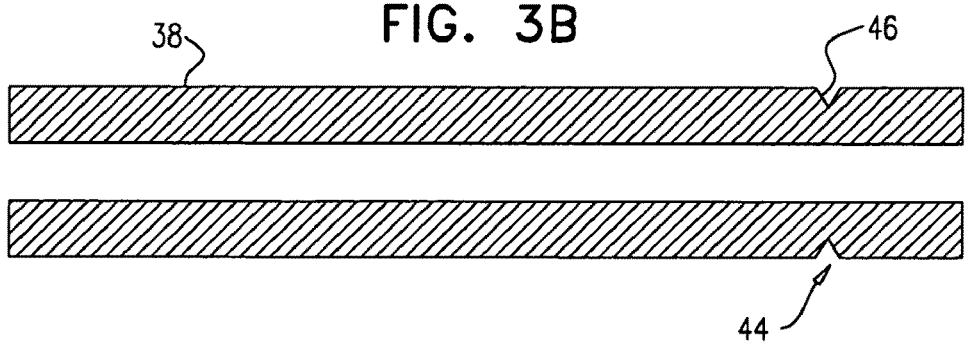
FIG. 3B a diagrammatic representation of an alternate exemplary delivery tube.
Figure 3C:
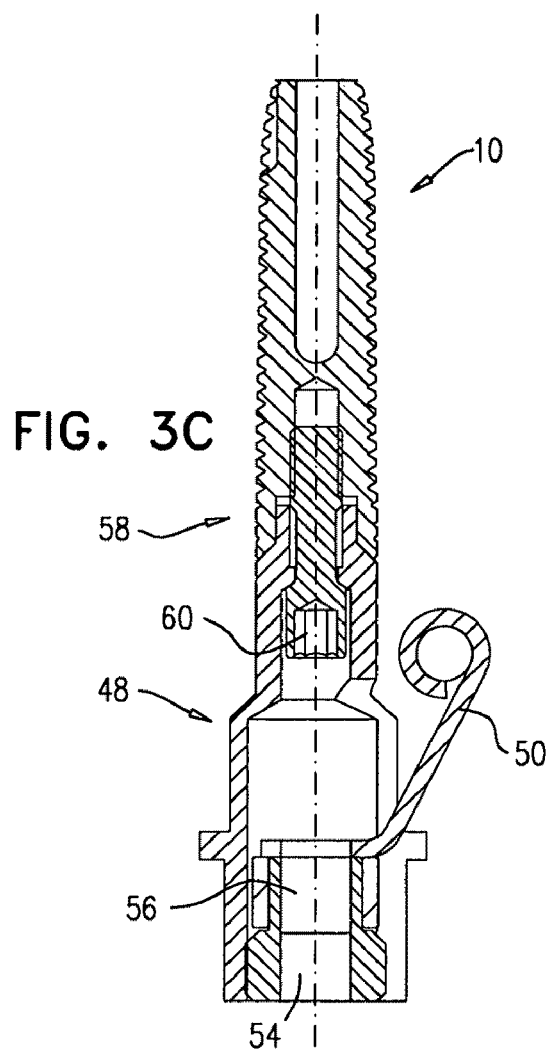
FIGS. 3C and 3D are diagrammatic representations of alternate views of the structure shown in FIG. 3A.

FIGS. 3A-C provide diagrammatic views of the apparatus/system 30 of FIG. 2. As depicted in FIG. 3A, a distal end of delivery tube 38 may be selectively connected to side inlet opening 22 of anchor 10 for directing fluid 36 into channel 18. Alternatively, a distal end of delivery tube 38 may form an integral connection 42 between the anchor 10 and delivery tube 38. The integral connection 42 may be configured such that it is to be permanently severed during implantation of anchor 10 in the bone of a subject. Such an integral connection 42 may be formed by bonding delivery tube 38 to side inlet opening 22 such as through known welding processes. The welding of delivery tube 38 to anchor 10 may provide a strong seal that is able to withstand the pressure of fluid 36 travelling therethrough.

Alternatively or in addition to integral connection 42, a wall of delivery tube 38 may include a region of weakened strength 44, as shown in FIG. 3A. This region of weakened strength 44 may be constructed so as to be thinner than a wall immediately adjacent to the region of weakened strength 44. Such a construction may ensure that upon application of a breaking torque, delivery tube 38 breaks at the region of weakened strength 44, thereby decoupling the delivery tube 38 from anchor 10. By way of example only, the region of weakened strength 44 may be within about 3 mm of the distal-most end of the delivery tube 38, such as within about 2 mm or within about 1 mm of the distal-most end of the delivery tube 38. Alternatively, the region of weakened strength 44 may be either less than or greater than 3 mm from the distal-most portion of the delivery tube 38.

Alternatively, as shown in FIG. 3B, the region of weakened strength 44 may include a groove 46 on delivery tube 38. Groove 46 may be configured so as to define a thinner region of the delivery tube 38. For example, groove 46 may be V-shaped, such that application of a breaking torque causes a concentration of force to be applied at the tip of the V, thereby severing delivery tube 38 at groove 46.

The region of weakened strength 44 of delivery tube 38 may be configured so that it is sufficiently thin that upon the application of a breaking torque of less than about 50 Newton centimeters (Ncm), delivery tube 38 severs at the region of weakened strength 44. By way of example only, the region of weakened strength 44 may have a width of less than about 0.1 mm, such as less than about 0.05 mm. Alternatively, the region of weakened strength 44 may have a width greater than about 0.1 mm.

In addition, the region of weakened strength 44 may be located beneath the outer surface of implant 10, in a direction toward central axis 24 of implant 10. With such a construction, any burrs that might result at locations of severance may be recessed from the outer surface of implant 10, minimizing risk of tissue damage when implant 10 is further advanced into the bone.

It is to be understood that the region of weakened strength 44 is not limited to the above features as depicted in FIGS. 3A-3B. Rather, it is envisioned that any structure capable of providing a region of weakened strength 44 may be used.

Delivery tube 38 may include a rigid material, such as a metal. More broadly, delivery tube 38 may include any material capable of severing at a region of weakened strength 44. Alternatively, delivery tube 38 may be mechanically disconnectable from inlet opening 22, such as through a friction fit or mechanical connector, enabling disconnection in manners other than severance.

Implant/apparatus system 30 may further include an applicator 48 which may be configured to sever delivery tube 38 at the region of weakened strength 44 by rotating the distal end of delivery tube 38 with respect to side inlet opening 22. For example, applicator 48 may be configured to apply a torque to the delivery tube 38 when the distal end of delivery tube 38 is rotated with respect to side inlet opening 22. For example, applicator 48 may be configured to apply the torque to delivery tube 38 without applying any meaningful torque to anchor 10 itself, and thus, does not dislodge or misalign anchor 10.

Figure 3D:
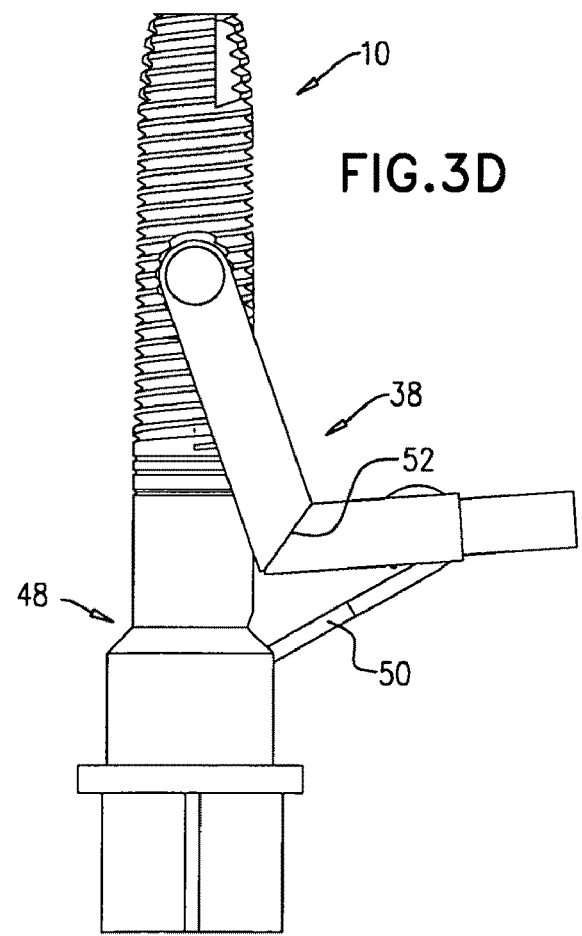

To facilitate severing, applicator 48 may include a lever arm 50, as shown in FIGS. 3C-3D. Lever arm 50 may be coupled to delivery tube 38 and configured to rotate the distal end of delivery tube 38 with respect to side inlet opening 22. For example, delivery tube 38 may be shaped so as to define a bend 52 at between about 5 mm and about 20 mm from the distal-most end of delivery tube 38, and lever arm 50 may be coupled to delivery tube 38 at a location proximal to bend 52 (FIG. 3D). In particular, bend 52 may include an angle of between about 85 and about 180 degrees.

Further, applicator 48 may comprise a rotatable surface 54 accessible from a proximal end of applicator 48, which is rotatable with respect to a portion of applicator 48. Rotation of rotatable surface 54 rotates the distal-most end of delivery tube 38 by extending lever arm 50. For example, rotation of the rotatable surface 54 may distally advance a transfer element 56 that may extend lever arm 50. In particular, rotatable surface 54 may define an internal hex, e.g., having an internal width of about 2.4 mm (the hex width is the distance between parallel sides of the hexagon). It is to be understood that other configurations are available to sever delivery tube 38 from the side inlet opening 22 and the configuration shown, and all dimensions, are for exemplary purposes only.

Further, applicator 48 may include a connecting element 58, which may removably couple applicator 48 to proximal end 14 of anchor 10. For example, connecting element 58 may include a connecting screw 60. As such, a head of connecting screw 60 may be accessible through a cavity that passes through rotatable surface 54, such that the head can be rotated with a screwdriver tool inserted through proximal end of the applicator 48, in order to decouple applicator 48 from anchor 10. In certain embodiments, connecting screw 60 may include an internal hex that has an internal width less than that of rotatable surface 54, e.g., about 1.25 mm. It is to be understood that the dimensions are for exemplary purposes only and the internal width of a hex may be greater or smaller than about 1.25 mm. Further, applicator 48 may be configured such that, in certain embodiments, rotation of rotatable surface 54 may both (a) apply the breaking torque to delivery tube 38 that may sever delivery tube 38 at the region of weakened strength 44, and (b) rotate connecting screw 60 to decouple applicator 48 from anchor 10.

Further, when delivery tube 38 is coupled to anchor 10 prior to severing at the region of weakened strength 44, a proximal portion 62 of delivery tube 38 may extend alongside anchor 10 such that, as shown in FIG. 3A, a greatest distance D between central axis 24 of anchor 10 and an external surface of proximal portion 62 of delivery tube 38 furthest from the central axis 24 is less than about 6 mm, such as less than about 5 mm. Such a distance may facilitate placement of anchor 10 and delivery tube 38 between adjacent teeth during an implantation procedure, such as described herein below with reference to FIGS. 5A-5F.

Alternatively, delivery tube 38 may be configured to sever from anchor 10 by any other appropriate means. For example, a surgeon or other user may sever delivery tube 38 from anchor 10 via any appropriate separate, external tool.

As mentioned previously, anchor 10 may include structure to facilitate its insertion into a bone of a subject. In particular, anchor 10 may include a self-tapping surface 64, including, for example, external thread 16 (FIG. 1A) in a region of the distal implant end 12. As shown in FIG. 1A, external thread 16, may extend at least along a portion of the lateral external surface of anchor 10. Alternatively, external thread 16 may extend along the entirety of anchor 10. Screw thread 16 may include a helical geometry or any other suitable geometry known in the industry. During rotation of the anchor 10, screw thread 16 allows anchor 10 to advance through a bone of a patient.

Figure 4A:
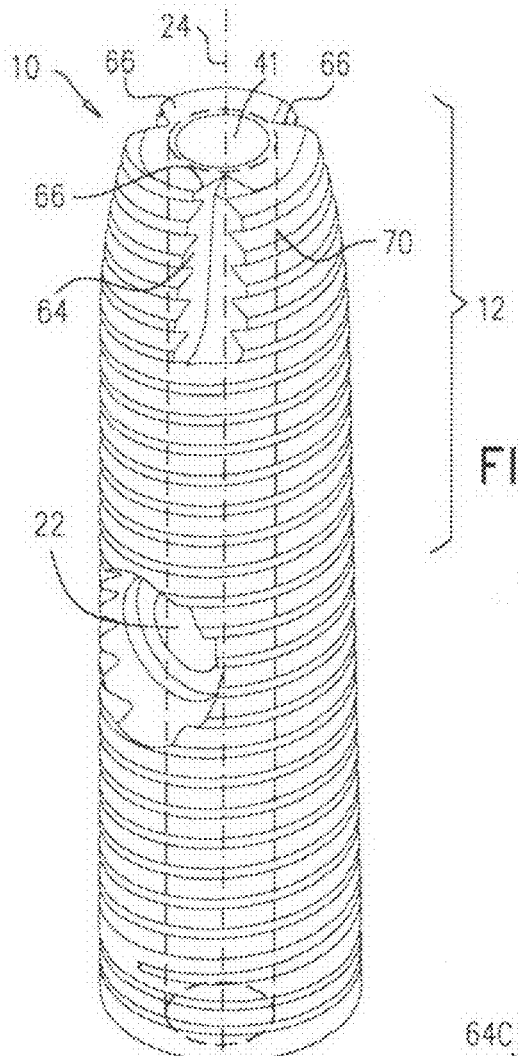
FIG. 4A provides a perspective view of the exemplary anchor of FIG. 1A.
Figure 4B:
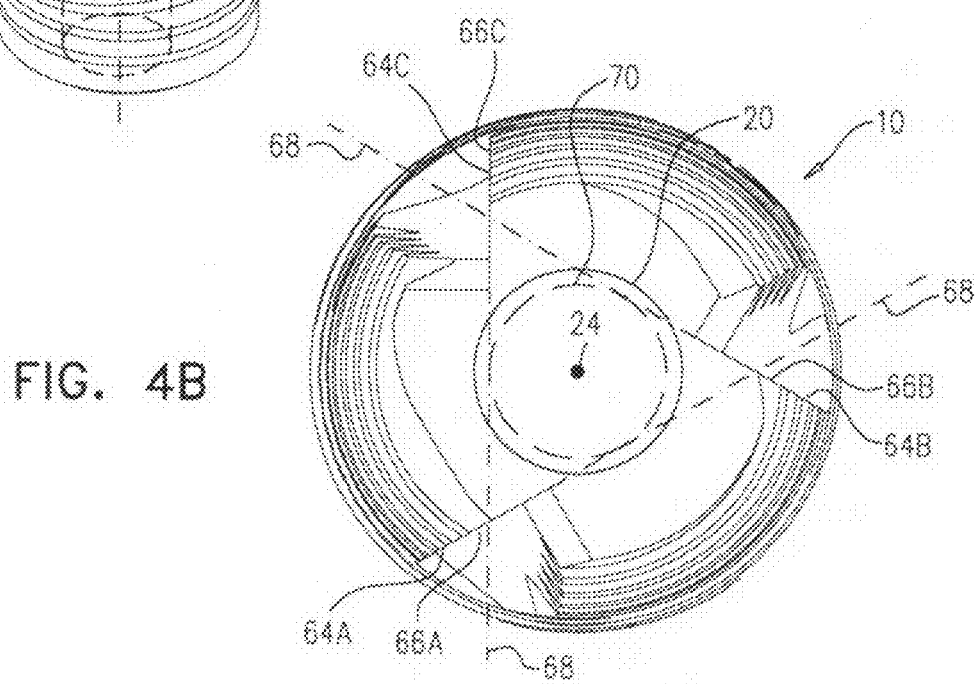
FIG. 4B provides a top view of the exemplary anchor of FIG. 1A.

In addition to self-tapping surface 64, as shown in FIGS. 4A and 4B, distal implant end 12 may include at least one end mill cutter surface 66 located adjacent outlet opening 20. End mill cutter surface 66 may be configured to break through bone and/or to grind bone. Alternatively, end mill cutter surface 66 may include a plurality of end mill cutter surfaces 66 which may be located in positions surrounding outlet opening 20 on distal implant end 12 of anchor 10. For some applications, for example, distal implant end 12 may be shaped so as to define two, three, four, five, or six end mill cutter surfaces 66. For example, in the configuration shown in FIGS. 4A and 4B, end mill cutter surface 66 defines exactly three cutting surfaces 66A, 66B, and 66C, i.e., is tripartite, and self-tapping surface 64 defines exactly three self-tapping surfaces 64A, 64B, and 64C. Surfaces 64 and 66 may be distributed evenly about a central axis 24 of anchor 10 and offset from central axis 24. Surfaces 66 may define lines 68, as shown in FIG. 4B. Lines 68 may be tangential to a circle 70 having a center which is intersected by central axis 24 of anchor 10. The circle 70 may or may not have the same radius as outlet opening 20. Thus, by way of non-limiting example, for applications in which end mill cutter surface 66 defines exactly two cutting surfaces 66A and 66B, lines 68 may be parallel to one another; for applications in which the end mill cutter surface 66 defines exactly three cutting surfaces 66A, 66B, and 66C, lines 68 may form a triangle; and, for applications in which the end mill cutter surface 66 defines exactly four cutting surfaces 66A, 66B, 66C, and 66D, lines 68 may form a square. It is contemplated that other configurations are available and are to be understood as within the scope of this disclosure.

The end mill cutter surface 66 may create bone fragments and bone dust during insertion of distal implant end 12 into a bone of a patient. Such bone fragments and bone dust may create a protective buffer of milled bone material. This protective buffer may be retained against distal implant end 12 of anchor 10. Such a configuration may allow the protective buffer of bone material to protect a Schneiderian membrane or periosteal tissue of a patient as the anchor 10 is advanced through the bone. In addition, end mill cutter surface 66 may grind the bone of the ridge, which is generally effective for breaking through bone. As such, distal portion 12 may both engage the lower portion of the bone while at the same time breaking through the upper portion of the bone.

In accordance with one embodiment of the invention there may be provided a method of implantation of a device in a bone of a subject. For example, the method may include a minimally invasive closed sinus lift surgical procedure for implanting anchor 10 in a bone of a subject. By way of example only, such a procedure may be performed when a patient's maxillary alveolar ridge lacks sufficient bone mass to support a conventional dental implant. While the method is described for exemplary purposes, as used to implant anchor 10 in a jaw or maxillary bone of a subject, the invention in its broadest sense is not so limited. Rather, it may be applied for use in any bone of a subject, whether human or animal.

A surgeon may begin the procedure by preparing the oral facial region and administering a local anesthetic. Optionally, as shown in FIG. 5A, the surgeon may initiate an osteotomy in a maxillary alveolar ridge 80 of a patient. Such an osteotomy may be made by initiating a bore in the alveolar ridge 80 with the aid of a dental implant drill, such as a conventional sinus bur 82. Alternatively, the initial bore may be formed by using any appropriate means to initiate such an opening in the alveolar ridge 80. Such a preliminary bore may have a diameter of between about 1 mm and about 7 mm, e.g., between about 2 and about 6 mm. It is to be understood that the bore may have any dimensions appropriate, and as such, it may have a diameter smaller than about 1 mm or larger than about 7 mm. Dimensions are provided for exemplary purposes only. Further, the initial bore may leave a residual bone thickness of between about 0.5 and about 5 mm, e.g., between about 1 and about 4 mm, or between about 0.5 and about 2 mm. Again, it is to be understood that the bore may have any dimensions appropriate, and as such, it may leave a residual bone thickness smaller than about 0.5 mm or larger than about 5 mm. Dimensions are provided for exemplary purposes only.

Optionally, a surgeon may widen the bore using a series of successively wider drill bits, until a desired bore diameter is achieved as determined by the specific application. For example, the largest drill bit may have a diameter of about 3.65 mm for an implant having a diameter of about 4.2 mm, or a diameter of about 4.2 mm for an implant having a diameter of about 5 mm. It is to be understood that alternative dimensions are deemed to be within the scope of the invention and dimensions are provided only for exemplary purposes only. The bore may be measured using any suitable technique known in the art, such as, by way of example only, depth guide, dental probe, CT imaging, x-ray imaging, or depth guide enhanced x-ray imaging, etc. Also, a surgical guide may be used to ensure clearance between the center of the osteotomy and the nearest tooth surface. Optionally, a pre-surgery radiograph (e.g., CT or x-ray) may be performed, in order to enable the surgeon to estimate the height of the residual bone and plan the osteotomy accordingly.

After drilling the preliminary bore, the surgeon may advance anchor 10 into the bore. The surgeon may advance anchor 10 by any appropriate means, such as, for example, by screwing anchor 10 into ridge 80 using a surgical screwing tool 32, as shown in FIG. 5B. Screwing tool 32 may comprise a conventional manual ratchet wrench, or a conventional drill or motor to which an appropriate drill head is attached, and which is operated at a controlled speed and at controlled torque. Alternatively, screwing tool 32 may include a conventional hexagonal tool with a knurled knob, such as a knurled hex screwdriver, and along its axis, a thin rod having a hexagonal head which fits into a female hexagonal socket defined by a proximal end of applicator 48. Alternatively, any appropriate tool known in the art may be used to advance anchor 10 into ridge 80.

While the surgeon screws anchor 10, container 40 depicted as a syringe, may optionally provide fluid 36 under monitored pressure to distal implant end 12 via inlet conduit 34, delivery tube 38, and channel 18. As mentioned previously, fluid 36 may comprise any biocompatible solution, for example water, saline, or gas such as air. Further, anchor 10 may function as a cork such that it may isolate a distal-most end of the bore from the oral cavity. Such isolation may allow relatively high pressure to develop in fluid 36 distal to anchor 10, having exited outlet opening 20, without being released to the oral cavity of a patient. Also, a drop in the pressure may be detected as distal implant end 12 forms an opening through the distal-most portion of ridge 80 to just below a Schneiderian membrane 86 of a patient. Such an advancement of anchor 10 may bring outlet opening 20 into fluid communication with a proximal-most surface of the membrane 86 as shown in FIG. 5B. Upon detection of the drop, the surgeon may cease advancing anchor 10 such that anchor 10 does not perforate membrane 86. At this stage in the procedure, distal implant end 12 may not necessarily pass through the proximal-most portion of ridge 80.

The drop in pressure may be detected using any appropriate equipment, for example, a separate pressure gauge 88. Such a gauge may be coupled to inlet conduit 34, as shown in FIG. 5B, or directly to the container 40 (configuration not shown), as is known in the art, e.g., the Viceroy™ Inflation Syringe (Merit Medical Systems, Inc., South Jordan, Utah). Alternatively, for applications in which container 40 includes a powered drug delivery device, the drop in pressure may be detected using a pressure gauge 88 integrated into the drug delivery device, as is known in the art (configuration not shown). Further, an output unit (not shown) may generate an output notifying the surgeon of the drop in pressure. The output may include any signal sufficient to notify the surgeon, for example, an audio or visual signal, etc. Alternatively or additionally, a display may be used to display an indication of a numerical value of the measured pressure.

In an alternative embodiment, container 40 may include a loss-of-resistance (LOR) syringe, such as known in the epidural art for locating an epidural space. As such, the surgeon may detect a drop in pressure by detecting a loss of resistance as distal implant end 12 forms an opening through the distal-most side of ridge 80 to just below Schneiderian membrane 88. For exemplary purposes only, the Episure AutoDetect LOR Syringe (Indigo Orb, Inc., Irvine, Calif., USA) and similar devices may be used.

Alternatively, instead of providing and measuring a pressure of a fluid, after the initial insertion of anchor 10 into the bore, the surgeon may use a periapical radiograph to estimate remaining distance from distal implant end 12 to the proximal side of the membrane 86. As such, the surgeon may rotate the anchor 10 to penetrate into a sinus 90, such as by rotating anchor 10 by a number of rotations equal to the remaining distance divided by a constant, e.g., 1.2 mm. The surgeon may perform an additional periapical radiograph to ensure that anchor 10 has penetrated into sinus 90.

Alternatively, to the above mentioned pressure monitoring techniques, the surgeon may introduce fluid 36 through anchor 10 without employing a pressure monitoring means.

As shown in FIG. 5C, the surgeon may gently lift and separate membrane 86 from distal-most side of ridge 80 into a sinus 90, by injecting a fluid 36, for example a biocompatible solution, from container 40 either under or not under controlled pressure via inlet conduit 34, delivery tube 38, and channel 18, so as to form a cavity 92 under the membrane 86 between ridge 80 and the membrane 86 (in FIG. 5C, the membrane is shown partially raised). As membrane 86 is raised, an output indicative of a numerical value of the measured pressure, and/or a warning output if the measured pressure crosses a threshold value may be generated as appropriate. An increase in the pressure may generally indicate that the membrane 86 is expanding and may perforate.

Further, the surgeon may inject sufficient fluid 36 into cavity 92 to inflate cavity 92 to a vertical height, for example, of between about 2 and about 20 mm from the distal-most side of ridge 80, such as between about 2 and about 11 mm, e.g., between about 2 and about 8 mm. Also, a measured volume of fluid 36 is injected in order to achieve the desired cavity height, such as between about 0.5 and about 6 ml of fluid, e.g., between about 1 and about 4 ml, or between about 2 and about 4 ml. It is to be understood that the invention is not limited to a cavity 92 having particular dimensions or volume. Rather, in accordance with one embodiment of the invention, cavity 92 may have any appropriate dimensions and/or volume sufficient to lift membrane 86 as determined by the particular application.

The fluid 36, such as water, saline, other liquid, or gas, may be drained from the cavity 92, and the surgeon may inject a second fluid 36' into cavity 92, as shown in FIG. 5D. This second fluid may include a regenerative material such as, for example, liquid or gel bone graft, blood, or BMP. Fluid 36' may be injected using any appropriate means. For example, fluid 36' may be injected using a syringe, an LOR syringe, a powered drug delivery device, or any other known device for injecting fluid. Optionally, as fluid 36' is injected into cavity 92, an output indicative of the pressure of fluid 36' may be generated as discussed hereinabove above.

The volume of fluid 36 injected into cavity 92 may be measured, at the step of the procedure described hereinabove with reference to FIG. 5C. Responsive to the measured volume, the surgeon may determine an amount of fluid 36' to inject into cavity 92 at the step of the procedure described hereinabove with reference to FIG. 5D. For example, the amount of fluid 36' may be approximately equal to the volume of injected fluid 36, or slightly greater or less than the volume of the injected fluid 36. As a result, waste of fluid 36' may be minimized, and the likelihood of perforating membrane 86 by injection of fluid 36' may be reduced.

Further, the surgeon may use a flexible wire such as a piston (not depicted) to help push the fluid 36' through inlet conduit 34, delivery tube 38, and/or channel 18. This technique may be helpful when the fluid 36' is viscous and thus difficult to inject using an ordinary syringe.

Alternatively, the surgeon may inject fluid 36', rather than fluid 36, to lift membrane 86, thereby combining the steps of the procedure described hereinabove with reference to FIGS. 5C and 5D. In this case, fluid 36' may constitute any suitable biocompatible liquid or combinations of biocompatible liquids. Alternatively, the surgeon may drain fluid 36 from cavity 92 and, rather than injecting fluid 36', may immediately advance anchor 10 though ridge 80. In such a configuration, anchor 10, upon further insertion into the ridge, will lift membrane 86 and retain it in an elevated state. Further, instead of draining fluid 36, the surgeon may maintain fluid 36 in cavity 92, thus retaining membrane 86 in a lifted state. In such a configuration, subsequent injection of fluid 36' may not be required, and anchor 10 may be advanced though ridge 80.

Thereafter, the surgeon may decouple delivery tube 38 from anchor 10, and further advance (e.g., by rotating or screwing) anchor 10 into fluid 36' in cavity 92, as shown in FIG. 5E. The surgeon may decouple delivery tube 38 before or while further advancing anchor 10, and/or by advancing anchor 10 until the tube becomes decoupled because of the rotation. Alternatively, the surgeon may use any means known in the art for decoupling delivery tube 38 from anchor 10, such as, for example, a separate external tool.

As shown in FIG. 5E, the additional advancing of anchor 10 into ridge 80 and fluid 36' may advance side inlet opening 22 of anchor 10 at least until side inlet opening 22 is positioned entirely within the bore in ridge 80 and/or in fluid 36' in cavity 92. Such positioning of anchor 10 may allow side inlet opening 22 and outlet opening 20 of channel 18 to reside entirely within bone and or fluid 36'. Such a configuration may substantially reduce the risk of infection, because proximal end 14 of anchor 10, which may otherwise be exposed to the oral cavity or gingival of a patient, may be permanently closed. The surgeon may then decouple applicator 48 from anchor 10, by any appropriate means in order to expose proximal end 14 of anchor 10 to the oral cavity or gingival of the patient.

As is known in the art, fluid 36', which, for example, can include regenerative material, may induce bone growth in the area of injection. Such bone growth may aid in supplementing the existing ridge 80. As shown in FIG. 5F, after bone grows into fluid 36' and is integrated into ridge 80, an appliance 94, such as a crown, may be coupled to anchor 10, typically using an abutment 96 coupled to anchor 10, as is known in the art. Alternatively, anchor 10 may include a single-stage transgingival implant/abutment, as is known in the art.

In the foregoing Description of Exemplary Embodiments, various features are grouped together in a single embodiment for purposes of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate embodiment of the invention.

Moreover, it will be apparent to those skilled in the art from consideration of the specification and practice of the present disclosure that various modifications and variations can be made to the disclosed apparatuses and methods without departing from the scope of the invention, as claimed. Thus, it is intended that the specification and examples be considered as exemplary only, with a true scope of the present disclosure being indicated by the following claims and their equivalents.

What is claimed is:

1. An implant apparatus, comprising:
    an anchor having a distal implant end and an opposite proximal end; and
    a channel extending through a portion of the anchor, the channel having an outlet opening in the distal implant end, and an inlet opening on a side of the anchor between the distal implant end and the proximal end, wherein the inlet opening, the channel, and the outlet opening are configured to convey fluid therethrough,
    wherein the implant is configured for implantation in, and the anchor is configured for insertion in, a jaw bone such that when fully implanted, the side inlet opening is buried in the jaw bone,
    further comprising an inlet conduit selectively connected to the side inlet opening for directing fluid into the channel through the side inlet opening.

2. The implant apparatus of claim 1, wherein the anchor is configured to alternatively assume a partially-implanted orientation and a fully-implanted orientation, wherein in the partially implanted orientation the side inlet opening is configured to protrude from the bone to permit access to the channel, and wherein in the fully-implanted orientation the side inlet opening is buried in the bone to block access to the channel.

3. The implant apparatus of claim 1, wherein the proximal end is configured so that a prosthesis is connectable thereto.

4. The implant apparatus of claim 3, wherein the proximal end is configured to permit a prosthetic tooth to be connected thereto when the anchor is in the fully inserted position.

5. The implant apparatus of claim 4, further comprising an integral connection between the anchor and the inlet conduit, the integral connection being configured to be permanently severed during an implantation procedure.

6. The implant apparatus of claim 5, wherein the integral connection includes a weld.

7. The implant apparatus of claim 5, wherein the integral connection is configured to sever at a location internally spaced from an external surface of the anchor.

8. The implant apparatus of claim 1, wherein the channel extends in a direction from the distal end toward the proximal end, and the inlet opening is spaced from the proximal end.

9. The implant apparatus of claim 1, wherein the anchor is configured so that when fully implanted, the inlet opening is completely located at least 1 mm within the jaw bone.

10. The implant apparatus of claim 1, wherein the anchor is configured so that when fully implanted, the inlet opening is completely located at least 3 mm within the jaw bone.

11. The implant apparatus of claim 1, further including at least one self-tapping surface located in a region of the distal implant end and at least one milling edge on the implant end adjacent to the outlet opening.

12. The implant apparatus of claim 11, wherein a plurality of milling edges bound the outlet opening in the distal end of the implant.

13. The implant apparatus of claim 11, wherein the at least one milling edge is configured to perform at least one of breaking through bone and grinding bone.

14. The implant apparatus of claim 11, wherein the anchor is configured to rotate within an osteotomy in the jaw bone and to mill an edge of the osteotomy as the implant is rotated.

15. The implant apparatus of claim 14, further including at least one thread formed on the anchor, and wherein the self-tapping surface, the at least one milling edge, and the at least one thread are configured to cooperate so that when fluid is conveyed through the channel during an implant procedure, the fluid is substantially prevented from leaking between the implant and the jaw bone.

16. The implant apparatus of claim 1, further comprising at least one milling edge on the implant end configured so that a protective buffer of milled bone material is retained against the distal end, and wherein the anchor is configured for insertion in a patient's maxillary jaw bone such that when the distal end breaks through the maxillary jaw bone the protective buffer protects a Schneiderian membrane from the distal end.

17. The implant apparatus of claim 16, wherein the distal end has a concave shape.

18. The implant apparatus of claim 1, further comprising a quantity of bone augmenting material and at least one conduit connectable to the side inlet opening and for conveying the bone augmenting material through the inlet opening in the side of the anchor.

19. The implant apparatus of claim 18, further comprising a syringe for containing the bone augmenting material.

20. The implant apparatus of claim 1, wherein the channel is not open through the proximal end.

21. The implant apparatus of claim 1, wherein the inlet conduit is configured to be disconnected from the side inlet opening after directing the fluid into the channel.

22. An implant apparatus, comprising:
an anchor having a distal implant end and an opposite proximal end; and
a channel extending through a portion of the anchor, the channel having an outlet opening in the distal implant end, and an inlet opening on a side of the anchor between the distal implant end and the proximal end, wherein the inlet opening, the channel, and the outlet opening are configured to convey fluid therethrough,
wherein the implant is configured for implantation in, and the anchor is configured for insertion in, a jaw bone such that when fully implanted, the side inlet opening is buried in the jaw bone,
wherein the anchor is configured to alternatively assume a partially-implanted orientation and a fully-implanted orientation, wherein in the partially implanted orientation the side inlet opening is configured to protrude from the bone to permit access to the channel, and wherein in the fully-implanted orientation the side inlet opening is buried in the bone to block access to the channel,
wherein the proximal end is configured to permit a prosthesis to be connected thereto when the anchor is in the fully inserted position, and
further comprising an inlet conduit configured to direct fluid into the channel through the side inlet opening and an integral connection between the anchor and the inlet conduit, the integral connection being configured to be permanently severed during an implantation procedure,
wherein the integral connection includes a weakened region, such that the inlet conduit is configured to sever from the anchor at the weakened region.

23. The implant apparatus of claim 22, wherein the weakened region includes a substantially V shaped groove.

24. The implant apparatus of claim 22, wherein the prosthesis comprises a prosthetic tooth, and wherein the proximal end is configured to permit the prosthetic tooth to be connected thereto when the anchor is in the fully inserted position.

25. An implant apparatus, comprising:
an anchor having a distal implant end and an opposite proximal end; and
a channel extending through a portion of the anchor, the channel having an outlet opening in the distal implant end, and an inlet opening on a side of the anchor between the distal implant end and the proximal end, wherein the inlet opening, the channel, and the outlet opening are configured to convey fluid therethrough,
wherein the implant is configured for implantation in, and the anchor is configured for insertion in, a jaw bone such that when fully implanted, the side inlet opening is buried in the jaw bone,
wherein the anchor is configured to alternatively assume a partially-implanted orientation and a fully-implanted orientation, wherein in the partially implanted orientation the side inlet opening is configured to protrude from the bone to permit access to the channel, and wherein in the fully-implanted orientation the side inlet opening is buried in the bone to block access to the channel,
wherein the proximal end is configured to permit a prosthesis to be connected thereto when the anchor is in the fully inserted position, and
further comprising:
an inlet conduit configured to direct fluid into the channel through the side inlet opening and an integral connection between the anchor and the inlet conduit, the integral connection being configured to be permanently severed during an implantation procedure; and
a lever, accessible from the proximal end, for permitting a user to exert force on and sever the integral connection.

26. The implant apparatus of claim 25, wherein the prosthesis comprises a prosthetic tooth, and wherein the proximal end is configured to permit the prosthetic tooth to be connected thereto when the anchor is in the fully inserted position.

27. An implant method, comprising:
drilling a hole in a maxillary bone;
inserting an implant into the hole in a manner forming a substantially liquid tight seal between the implant and the maxillary bone; and
lifting a Schneiderian membrane by introducing fluid through a channel in the implant such that the fluid contacts the Schneiderian membrane and exerts a force thereon, causing a space between the maxillary bone and the Schneiderian membrane,
wherein the introducing fluid includes introducing fluid through a side inlet opening in the implant, and further comprising subsequently further inserting the implant into the maxillary bone such that the side inlet opening is buried inside the bone.

28. The method of claim 27, further comprising draining the fluid from the space via the channel in the implant.

29. The method of claim 27, further including milling bone material and retaining milled bone material adjacent a distal end of the implant to form a protective buffer between the distal end and the Schneiderian membrane.

30. The method of claim 27, further comprising conveying bone regenerative material through the channel and into the space.

* * * * *